(12) United States Patent
Ringlien

(10) Patent No.: US 8,896,828 B2
(45) Date of Patent: Nov. 25, 2014

(54) OPTICAL INSPECTION OF CONTAINERS

(75) Inventor: James A. Ringlien, Maumee, OH (US)

(73) Assignee: Owens-Brockway Glass Container Inc., Perrysburg, OH (US)

(*) Notice: Subject to any disclaimer, the term of this patent is extended or adjusted under 35 U.S.C. 154(b) by 415 days.

(21) Appl. No.: 13/074,789

(22) Filed: Mar. 29, 2011

(65) Prior Publication Data

US 2012/0250012 A1 Oct. 4, 2012

(51) Int. Cl.
*G01N 21/51* (2006.01)
*G01N 21/958* (2006.01)
*G01N 21/90* (2006.01)
*B07C 5/34* (2006.01)

(52) U.S. Cl.
CPC .......... *B07C 5/3408* (2013.01); *G01N 21/9072* (2013.01)
USPC .................. 356/239.4; 356/239.1; 250/223 B

(58) Field of Classification Search
USPC .............................. 356/239.4, 240.1; 382/142
See application file for complete search history.

(56) References Cited

U.S. PATENT DOCUMENTS

| | | | |
|---|---|---|---|
| 4,435,641 A | 3/1984 | Hajime | |
| 4,580,045 A * | 4/1986 | Kulig | 250/223 B |
| 4,852,415 A * | 8/1989 | Bogatzki et al. | 73/865.8 |
| 5,461,228 A | 10/1995 | Kirkman et al. | |
| 5,486,693 A | 1/1996 | Achter et al. | |
| 5,661,294 A | 8/1997 | Buchmann et al. | |
| 7,010,863 B1 | 3/2006 | Juvinall et al. | |
| 7,329,855 B2 | 2/2008 | Katayama et al. | |
| 7,330,251 B2 | 2/2008 | Katayama et al. | |

FOREIGN PATENT DOCUMENTS

JP 57-064153 * 4/1982 ............. G01N 21/88

OTHER PUBLICATIONS

International Search Report and Written Opinion, International Application No. PCT/US2012/031217, International Filing Date: Mar. 29, 2012, Mailing Date: Jun. 13, 2012, pp. 11.

* cited by examiner

*Primary Examiner* — Tarifur Chowdhury
*Assistant Examiner* — Rebecca C Bryant

(57) ABSTRACT

An apparatus and method for inspecting a container having a mouth, and a base with a punt opposite of the container mouth. Light energy is directed into the container and through the container mouth, using at least one light source, and light energy transmitted through the container mouth is sensed. The at least one light source is disposed on at least one side of the container so that the light energy is directed through a side wall of the container and onto the punt of the container base such that at least a portion of the light energy is reflected off the punt to extend through the container mouth to the light sensor.

10 Claims, 1 Drawing Sheet

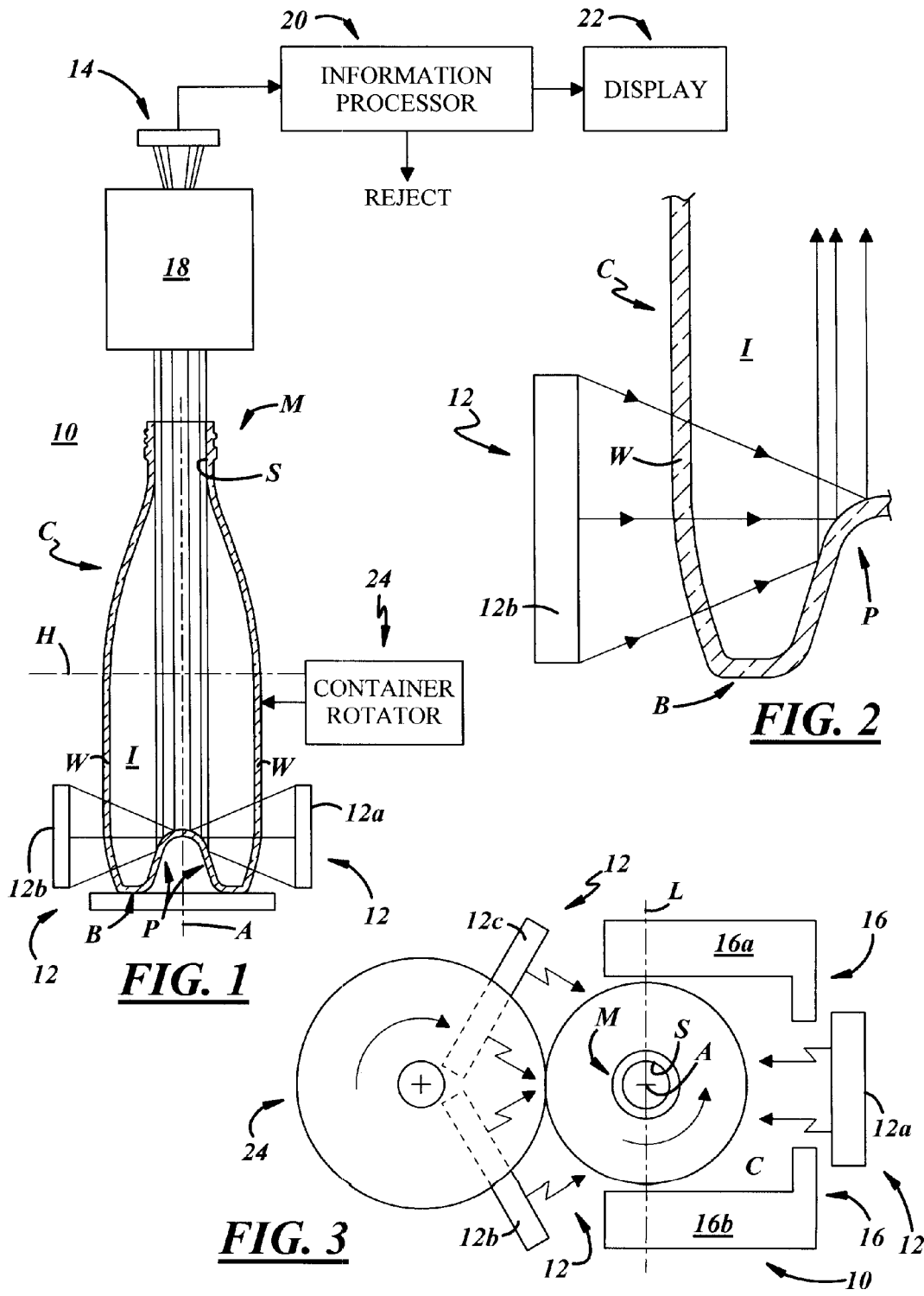

OPTICAL INSPECTION OF CONTAINERS

The present disclosure is directed to methods and apparatus for optical inspection of containers.

BACKGROUND AND SUMMARY OF THE DISCLOSURE

In the manufacture of containers, various anomalies or variations can occur that affect the commercial acceptability of the containers. These anomalies, termed "commercial variations," can involve numerous attributes of the container. For example, commercial variations can include dimensional characteristics of an open mouth of the container. Thus, it is oftentimes useful to provide inspection equipment capable of inspecting the containers for commercial variations. The term "inspection" is used in its broadest sense to encompass any optical, electro-optical, mechanical or electrical observation or engagement with a container to measure or determine a potentially variable characteristic, including but not necessarily limited to commercial variations.

Apparatuses for inspecting parameters of a container mouth are used in one type of inspection process for a container. Such an apparatus includes a light source that directs light energy into the container, and a light sensor disposed with respect to the light source and the container to receive light energy transmitted out of the container through the container mouth. A telecentric lens directs onto the light sensor only light energy transmitted through the container mouth substantially axially of the container mouth. The sensor develops a two-dimensional image of the container mouth, and is coupled to image processing electronics for determining or calculating a circle of greatest diameter that will fit within the two-dimensional image of the container mouth, and treating such circle as indicative of the effective inside diameter of the container mouth. An apparatus of this type is illustrated by U.S. Pat. No. 5,461,228, which is assigned to the assignee hereof and is incorporated herein by reference.

A general object of the present disclosure, in accordance with one aspect of the disclosure, is to provide an optical plug gage (OPG) apparatus effective for improving inspection of a mouth of a container having a punt in a bottom of the container.

The present disclosure embodies a number of aspects that can be implemented separately from or in combination with each other.

An apparatus for inspecting a container having a mouth, and a base with a punt opposite the container mouth, in accordance with one aspect of the disclosure includes at least one light source for directing light energy into the container, and out of the container through the container mouth, and a light sensor disposed with respect to the at least one light source and the container to receive light energy transmitted through the container mouth. The at least one light source is disposed on at least one side of the container so that the light energy is directed through a side wall of the container and onto the punt of the container base such that at least a portion of the light energy is reflected off the punt to extend through the container mouth to the light sensor.

In accordance with another aspect of the disclosure, there is provided a method of inspecting a container having a mouth, and a base with a punt opposite the container mouth, including the steps of directing light energy into the container, and out of the container through the container mouth, using at least one light source, and sensing light energy transmitted through the container mouth. The at least one light source is disposed on at least one side of the container so that the light energy is directed through a side wall of the container and onto the punt of the container base such that at least a portion of the light energy is reflected off the punt to extend through the container mouth to the light sensor.

In accordance with a further aspect of the disclosure, there is provided a method of inspection, including the steps of providing a container having a mouth and a base with a punt opposite the container mouth, and directing light energy into the container, and out of the container through the container mouth, using at least one light source. The method also includes the step of sensing light energy transmitted through the container mouth, wherein the at least one light source is disposed on at least one side of the container so that the light energy is directed through a side wall of the container and onto the punt of the container base such that at least a portion of the light energy is reflected off the punt to extend through the container mouth to the light sensor.

BRIEF DESCRIPTION OF THE DRAWINGS

The disclosure, together with additional objects, features, advantages and aspects thereof, will be best understood from the following description, the appended claims and the accompanying drawings, in which:

FIG. 1 is a schematic diagram of an optical plug gage apparatus for evaluating a mouth of a container in accordance with an exemplary embodiment of the present disclosure, and including a light source;

FIG. 2 is an enlarged fragmentary view of a portion of the apparatus and container of FIG. 1; and FIG. 3 is a schematic top view of a portion of the apparatus of FIG. 1.

DETAILED DESCRIPTION OF PREFERRED EMBODIMENTS

FIG. 1 illustrates an exemplary embodiment of an optical plug gage apparatus 10 for inspecting an inside surface S of an open mouth M of a container C. The apparatus 10 includes one or more light sources 12 disposed adjacent the container C on sides thereof to produce light used in inspecting the container mouth M, and one or more light sensors 14 disposed above the container C to sense light produced by the light source 12 and passing through the container mouth M. The apparatus 10 further may include a lens system 18 disposed between the container C and the light sensor 14 to direct light passing through the container mouth M to the light sensor 14. The apparatus 10 additionally may include a processor 20 to scan the light sensor 14 and develop an image of the container mouth M and/or any other suitable inspection information, and a display 22 to display the image and/or other inspection information. The apparatus 10 also may include a container rotator 24 to rotate the container C. As shown in FIG. 3, a material handling mechanism 16 may be constructed and arranged to move the container C.

The container C may be ajar, or a bottle as illustrated in FIG. 1, or any other suitable type of container that includes a base B having a punt P that may be disposed axially opposite of the container mouth M. Bottles having a punt P are common for packaging wine. The punt P may have a height, extending from the bottom of the base B to the top of the punt P, that typically is about 20% to about 80% of the outside diameter of the container C. The container C may be composed of plastic, glass, or any other suitable material. The container C may be clear, colored, transparent, translucent, or of any other suitable optical quality.

As shown in FIG. 3, the material handling mechanism 16 may include opposed legs 16a, 16b between which the container C is disposed and moved by the mechanism 16 in any suitable manner. The mechanism 16 may be a star wheel or any other suitable container handling device, and its legs 16a, 16b may be disposed at any suitable elevation with respect to the container.

As also shown in FIG. 3, the light source 12 may include a plurality of discrete sources 12a, 12b, 12c. For example, the light source 12 may include one side source 12a on one side of the container C, and two other side sources 12b, 12c disposed adjacent to each on another side of the container C generally opposite that of the one side source 12a. An imaginary line L bisects the container C into two sides. The one side source 12a may be disposed between the opposed legs 16a, 16b of the material handling mechanism 16. The other side sources 12b, 12c may be disposed beneath the container rotator 24, between the rotator 24 and the container base B (FIG. 1). Accordingly, the side sources 12a, 12b, 12c may be sized and arranged about the circumference of the container C to each illuminate a portion, for example about twenty to forty angular degrees, of the circumference of the punt P. Accordingly, the container C may be rotated by the rotator 24 to provide full circumferential illumination, wherein several images of portions of the container mouth M may be obtained and superimposed or added to produce a composite image of the container mouth M. Those of ordinary skill in the art will recognize that more or less than the three side sources 12a, 12b, 12c may be used.

The light source 12 may include any suitable type of device, including a plurality of light emitting diodes (LEDs), incandescent bulbs, fluorescent bulbs, or any other suitable type of light source. In any case, those of ordinary skill in the art will recognize that the light source 12 may receive power from any suitable source in any suitable manner and may be communicated to and controlled by the processor 20 in any suitable manner. Moreover, those of ordinary skill in the art will recognize that the light source 12 may be composed of any suitable quantity of individual light sources instead of just the three sources 12a, 12b, 12c.

Preferably, with respect to FIG. 1, the light source 12 is not disposed adjacent an upper half of the container C above a half-height line H bisecting the container C, or beneath the base B of the container C. Such positioning of the light source 12 was discovered to result in excessive absorption of light by the walls of the container C and/or refractions/reflections off interior surfaces of the container C. Such excessive absorption and/or refractions/reflections can result in false, inconclusive, or otherwise unreliable inspection results.

Instead, it was discovered, that the light source 12 may be disposed adjacent to the base B of the container C, and adjacent a bottom half of the container C below the half-height line H. More particularly, the light source 12 may be generally positioned in correspondence to, the punt P of the container C as shown in FIGS. 1 and 2. For example, the light source 12 may be axially centered on and/or axially overlapping with respect to the punt P. Accordingly, the light source 12 is constructed and arranged to target or selectively illuminate the punt P. Also, the light source 12 may be oriented in a generally transverse direction with respect to the longitudinal axis A of the container C as shown in FIGS. 1 and 2. More particularly, the source 12 may be oriented substantially perpendicularly with respect to the container axis A. As used herein, the term "substantially" means within typical glass container manufacturing and equipment setup tolerances. One or more of the above light source positions and/or orientations are believed to reduce or eliminate the excessive absorption and/or refractions/reflections to result in more reliable inspection results.

Still referring to FIG. 1, the light sensor 14 may include any suitable device to sense light. For example, the light sensor 14 may include an image sensor, for instance, a charge-coupled device (CCD), complementary metal-oxide-semiconductor (CMOS) device, or any other suitable image sensor. In another example, the light sensor 14 may include a photo-diode device, a photoresistor device, or any other suitable photodetector device.

The lens system 18 may include any suitable device to direct or focus light. For example, the lens system 18 may include a telecentric lens, an entrance pupil, and pupil lenses on either side of the pupil. The lens system 18 may direct only light rays that emerge from the container mouth M essentially parallel to an axis A of the container C.

The processor 20 may include any suitable device(s) to acquire images from the light sensor 14 and output images to the display 22.

The container rotator 24 may include any suitable device to rotate the container C. For example, the rotator 24 may include one or more rollers, wheels, belts, discs, and/or any other suitable element(s) to rotate the container C. In another embodiment, the container C may remain stationary, and one or more of the various apparatus elements 12, 14, 16, 18 may be rotated in any suitable manner.

Referring now to FIG. 3, and with regard to the material handling mechanism 16 and container rotator 24, an example of an indexing and inspection machine that may utilize the optical inspection apparatus and method of the present disclosure is shown in U.S. Pat. No. 6,581,751, which is incorporated herein by reference. The machine disclosed in that patent receives a continuous stream of glass articles from an infeed conveyer and transports the articles through a series of angularly spaced inspection stations, each of which examines the container according to different criteria. The indexing and inspection machine includes a first array of gripping fingers mounted on a lower carrier, and a second array of gripping fingers mounted on an upper carrier. Rotation of the carriers with respect to each other causes the finger arrays to grip and release the glassware articles between the individual fingers, while rotation of the carriers conjointly causes them to index the glassware between inspection stations. At least some of the inspection stations include drive rollers for rotating a container about its axis for inspection or other purposes.

Another example of an indexing and inspection machine that could utilize the optical inspection apparatus and method of the present invention is disclosed in U.S. Pat. No. 3,313,409, which is incorporated herein by reference. The apparatus disclosed in that patent uses a belt conveyer to transport containers along a guideway. In general operation, the containers encounter an indexing head that is circular and has a plurality of circumferentially spaced pockets for receiving the containers. The indexing head is successively indexed to bring each container into position in adjacent inspection stations, which may inspect the containers for various commercial variations and/or other characteristics. After the container has been inspected by each inspection station, the container encounters a discharge station which ejects it onto a conveyer for carrying the container away from the machine. Of course, the above-mentioned patents disclose only two examples of machines that may employ the optical inspection apparatus and method of the present invention, as numerous other machines also exist.

In one example of operation of the presently disclosed apparatus 10, the light source 12 is energized, and at least some of the light from the side sources 12a, 12b, 12c travels through an outer wall W of the container C, into the container C, and reflects off the punt P extending parallel to the container axis A and through the container mouth M. More particularly, the light reflects off a surface of the punt P disposed within an interior I (FIG. 1) of the container C. The light traveling through the container mouth M is sensed by the light sensor 14 to obtain a corresponding image of the container mouth M.

There thus has been disclosed an apparatus and method for optical inspection of a container, that fully satisfies all of the objects and aims previously set forth. The disclosure has been presented in conjunction with several exemplary embodiments, and additional modifications and variations have been discussed. Other modifications and variations readily will suggest themselves to persons of ordinary skill in the art in view of the foregoing discussion. The disclosure is intended to embrace all such modifications and variations as fall within the spirit and broad scope of the appended claims.

The invention claimed is:

1. An apparatus for inspecting a container, said apparatus including:
    a container having a mouth and a base with a punt opposite the mouth, wherein the punt extends into the interior volume of the container;
    at least one light source for directing light energy into the container, off at least a portion of the punt extending into the interior volume of the container, and out of the container through the container mouth; and
    a light sensor disposed with respect to said at least one light source and the container to receive light energy transmitted through the container mouth,
    wherein said at least one light source is disposed on at least one side of the container so that said light energy is directed through a side wall of the container and onto the punt of the container base such that at least a portion of the light energy is reflected off the punt to extend through the container mouth to said light sensor, and said at least one light source is disposed adjacent to, but not beneath, the container base and adjacent to a bottom half of the container below a half-height line bisecting the height of the container but not adjacent to an upper half of the container above the half-height line, and said at least one light source is oriented in a generally transverse direction with respect to a longitudinal axis of the container, and said at least one light source is generally positioned such that it axially overlaps at least a portion of the punt extending into the interior volume of the container.

2. The apparatus set forth in claim 1 wherein said at least one light source includes at least two light sources on one side of the container and at least one other light source on a generally opposite side of the container wherein the light sources are disposed substantially perpendicularly with respect to the longitudinal axis of the container.

3. The apparatus set forth in claim 1, including a container rotator to rotate the container about the longitudinal axis of the container to different angular positions and wherein said at least one light source is disposed beneath the container rotator, between the container rotator and the container base.

4. The apparatus set forth in claim 1, including a material handling mechanism having at least two legs between which the container is disposed, and wherein said at least one light source includes one side light source disposed between said at least two legs of said material handing mechanism.

5. The apparatus set forth in claim 4, wherein the material handling mechanism is a star wheel.

6. A method of inspecting a container having a mouth, and a base with a punt opposite the container mouth, including the steps of:
    directing light energy into the container, off at least a portion of the punt extending into the interior volume of the container, and out of the container through the container mouth, using at least one light source; and
    sensing light energy transmitted through the container mouth,
    wherein said at least one light source is disposed on at least one side of the container so that said light energy is directed through a side wall of the container and onto the punt of the container base such that at least a portion of the light energy is reflected off the punt to extend through the container mouth to said light sensor, and said at least one light source is disposed adjacent to, but not beneath, the container base and adjacent to a bottom half of the container below a half-height line bisecting the height of the container but not adjacent to an upper half of the container above the half-height line, and said at least one light source is oriented in a generally transverse direction with respect to a longitudinal axis of the container, and said at least one light source is generally positioned such that it axially overlaps at least a portion of the punt extending into the interior volume of the container.

7. The method set forth in claim 6 wherein said at least one light source includes at least two light sources on one side of the container and at least one other light source on an opposite side of the container wherein the light sources are disposed substantially perpendicularly with respect to the longitudinal axis of the container.

8. The method set forth in claim 6, including rotating the container about the longitudinal axis of the container to different angular positions and wherein said at least one light source is disposed beneath the container rotator, between the container rotator and the container base.

9. The method set forth in claim 6, including handling the container with a material handing mechanism having at least two legs between which the container is disposed, and wherein said at least one light source includes one side light source disposed between said at least two legs of said material handing mechanism.

10. A method of inspection, including the steps of:
    providing a container having a mouth and a base with a punt opposite the container mouth;
    directing light energy into the container, off at least a portion of the punt extending into the interior volume of the container, and out of the container through the container mouth, using at least one light source; and
    sensing light energy transmitted through the container mouth,
    wherein said at least one light source is disposed on at least one side of the container so that said light energy is directed through a side wall of the container and onto the punt of the container base such that at least a portion of the light energy is reflected off the punt to extend through the container mouth to said light sensor, and said at least one light source is disposed adjacent to, but not beneath, the container base and adjacent to a bottom half of the container below a half-height line bisecting the height of the container but not adjacent to an upper half of the container above the half-height line, and said at least one light source is oriented in a generally transverse direction with respect to the longitudinal axis of the container, and said at least one light source is generally positioned such that it axially overlaps at least a portion of the punt extending into the interior volume of the container.

* * * * *